(12) United States Patent
Kitagaki

(10) Patent No.: US 11,504,092 B2
(45) Date of Patent: Nov. 22, 2022

(54) ULTRASONIC PROBE AND ULTRASONIC DIAGNOSTIC APPARATUS

(71) Applicant: Konica Minolta, Inc., Tokyo (JP)

(72) Inventor: Ikuhiro Kitagaki, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 792 days.

(21) Appl. No.: 16/295,369

(22) Filed: Mar. 7, 2019

(65) Prior Publication Data

US 2019/0307424 A1    Oct. 10, 2019

(30) Foreign Application Priority Data

Apr. 9, 2018  (JP) .............................. JP2018-074885

(51) Int. Cl.
    *A61B 8/00*   (2006.01)
    *G01S 15/89*  (2006.01)
    *B06B 1/06*   (2006.01)
    *G01N 29/24*  (2006.01)

(52) U.S. Cl.
    CPC ............ *A61B 8/4494* (2013.01); *A61B 8/546* (2013.01); *B06B 1/0622* (2013.01); *G01N 29/2437* (2013.01); *G01S 15/8909* (2013.01); *G01S 15/8911* (2013.01)

(58) Field of Classification Search
    CPC .................... B06B 1/0622; G01N 29/2437
    See application file for complete search history.

(56) References Cited

U.S. PATENT DOCUMENTS

| 2003/0189391 A1* | 10/2003 | Shimizu ............... B06B 1/0622 310/334 |
| 2007/0276248 A1* | 11/2007 | Saito ..................... A61B 8/546 600/459 |
| 2010/0198077 A1* | 8/2010 | Ooura .................... A61B 8/08 600/459 |
| 2013/0134834 A1* | 5/2013 | Yoshikawa .......... H01L 41/053 310/341 |

FOREIGN PATENT DOCUMENTS

| EP | 2617497 A1 * | 7/2013 | .......... A61B 8/4494 |
| JP | S59-225045 A | 12/1984 | |
| JP | 2005-347804 A | 12/2005 | |
| JP | 2006-033801 A | 2/2006 | |
| JP | 2017-099504 A | 6/2017 | |

OTHER PUBLICATIONS

JPO, Office Action for the corresponding Japanese application No. 2018-074885, dated Sep. 28, 2021, with English translation.

* cited by examiner

*Primary Examiner* — Bryan P Gordon
(74) *Attorney, Agent, or Firm* — Lucas & Mercanti, LLP

(57) ABSTRACT

An ultrasonic probe includes: a piezoelectric element that is used for transmitting and receiving ultrasonic waves; a signal electrode that is disposed at a rear surface side of the piezoelectric element; and a backing that is disposed at a rear surface side of the signal electrode, wherein the backing has a thermal resistance of 8 K/W or less, and the backing attenuates an ultrasonic wave with the lowest frequency by 10 dB or more, among frequencies at which transmittance and reception sensitivity of the ultrasonic probe is decreased from the maximum value thereof by 20 dB.

6 Claims, 4 Drawing Sheets

ULTRASONIC PROBE AND ULTRASONIC DIAGNOSTIC APPARATUS

The entire disclosure of Japanese patent Application No. 2018-074885, filed on Apr. 9, 2018, is incorporated herein by reference in its entirety.

BACKGROUND

Technological Field

The present invention relates to an ultrasonic probe and an ultrasonic diagnostic apparatus.

Description of the Related Art

An ultrasonic diagnostic apparatus enables a shape, movement, and the like of tissues to be obtained as ultrasonic diagnostic images with a simple operation that an ultrasonic probe, which is connected to the ultrasonic diagnostic apparatus or is configured to be communicable with the ultrasonic diagnostic apparatus, is brought into contact with a body surface of a subject including a human, other animals, and the like or is inserted into the body. The ultrasonic diagnostic apparatus has an advantage that inspection can be repeatedly performed because of high safety of the apparatus.

The ultrasonic probe has a piezoelectric element transmitting and receiving ultrasonic waves, and the like built-in. The piezoelectric element receives an electric signal (transmission signal) from the ultrasonic diagnostic apparatus, converts the received transmission signal into an ultrasonic signal, transmits the ultrasonic signal, receives ultrasonic waves reflected in the living body, converts the ultrasonic waves into an electric signal (reception signal), and transmits the reception signal converted into the electric signal to the ultrasonic diagnostic apparatus.

Further, the ultrasonic probe has a backing in a direction opposite to a subject in relation to the piezoelectric element (incidentally, hereinafter, regarding a member constituting the ultrasonic probe, a surface facing a direction closer to the subject is also referred to the "front surface," and a surface facing a direction farther from the subject is also referred to as the "rear surface"). The backing attenuates (including, absorbs and scatters) ultrasonic waves transmitted from the piezoelectric element to the rear surface side and suppresses, for example, occurrence of noise (artifact) caused by the ultrasonic waves transmitted to the rear surface side being reflected from a backing end face. Further, the backing releases heat from the piezoelectric element to the rear surface side and suppresses overheat or the like of an acoustic lens being in contact with the subject, which is caused by heat generated in the piezoelectric element.

Herein, the magnitude of "attenuation" is determined by the shape (thickness) and the attenuation rate of the backing. As the attenuation of the backing increases (the thickness of the backing increases), it is possible to reduce reflection of ultrasonic waves from the rear surface side of the piezoelectric body.

An attempt for enhancing radiation properties of the backing is known. In an ultrasonic probe described in JP 2005-347804 A, a plurality of thin plates of thermal conductors are arranged with a constant interval in a backing material of a vibration unit or a plurality of linear members of thermal conductors are arranged with a constant interval in the backing material.

An ultrasonic probe described in JP 2017-99504 A includes a ultrasonic vibrator that transmits ultrasonic waves, a reflecting layer that is provided at a surface of the ultrasonic vibrator opposite to a subject side and reflects ultrasonic waves transmitted from the ultrasonic vibrator, and a backing layer that is provided at a side of the reflecting layer opposite to the ultrasonic vibrator side and is formed by a material having a thermal conductivity of 100 W/(m·K) or more.

In the ultrasonic probe, both of the radiation properties being increased and the ultrasonic attenuation properties being increased to suppress reflection of ultrasonic waves transmitted to the rear surface side are required.

In the ultrasonic probe described in JP 2005-347804 A, since those obtained by sandwiching the thin plates of thermal conductors with the backing materials are incorporated as the backing parts in the ultrasonic probe, sound is reflected inside the thin plates of thermal conductors sandwiched with the backing materials and ultrasonic waves cannot be sufficiently attenuated. Further, since the ultrasonic probe described in JP 2017-99504 A has the backing containing graphite or the like, ultrasonic waves cannot be sufficiently attenuated. For those reasons, in order to suppress degradation in image quality due to the influence of reflection from the backing, a reflecting layer needs to be disposed between the ultrasonic vibrator and the backing layer.

SUMMARY

An object of the present invention is to provide an ultrasonic probe and an ultrasonic diagnostic apparatus that are capable of increasing both radiation properties and ultrasonic attenuation properties.

To achieve the abovementioned object, according to an aspect of the present invention, an ultrasonic probe reflecting one aspect of the present invention comprises: a piezoelectric element that is used for transmitting and receiving ultrasonic waves; a signal electrode that is disposed at a rear surface side of the piezoelectric element; and a backing that is disposed at a rear surface side of the signal electrode, wherein the backing has a thermal resistance of 8 K/W or less, and the backing attenuates an ultrasonic wave with the lowest frequency by 10 dB or more, among frequencies at which transmittance and reception sensitivity of the ultrasonic probe is decreased from the maximum value thereof by 20 dB.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

(Ultrasonic Probe)

Figure 1:
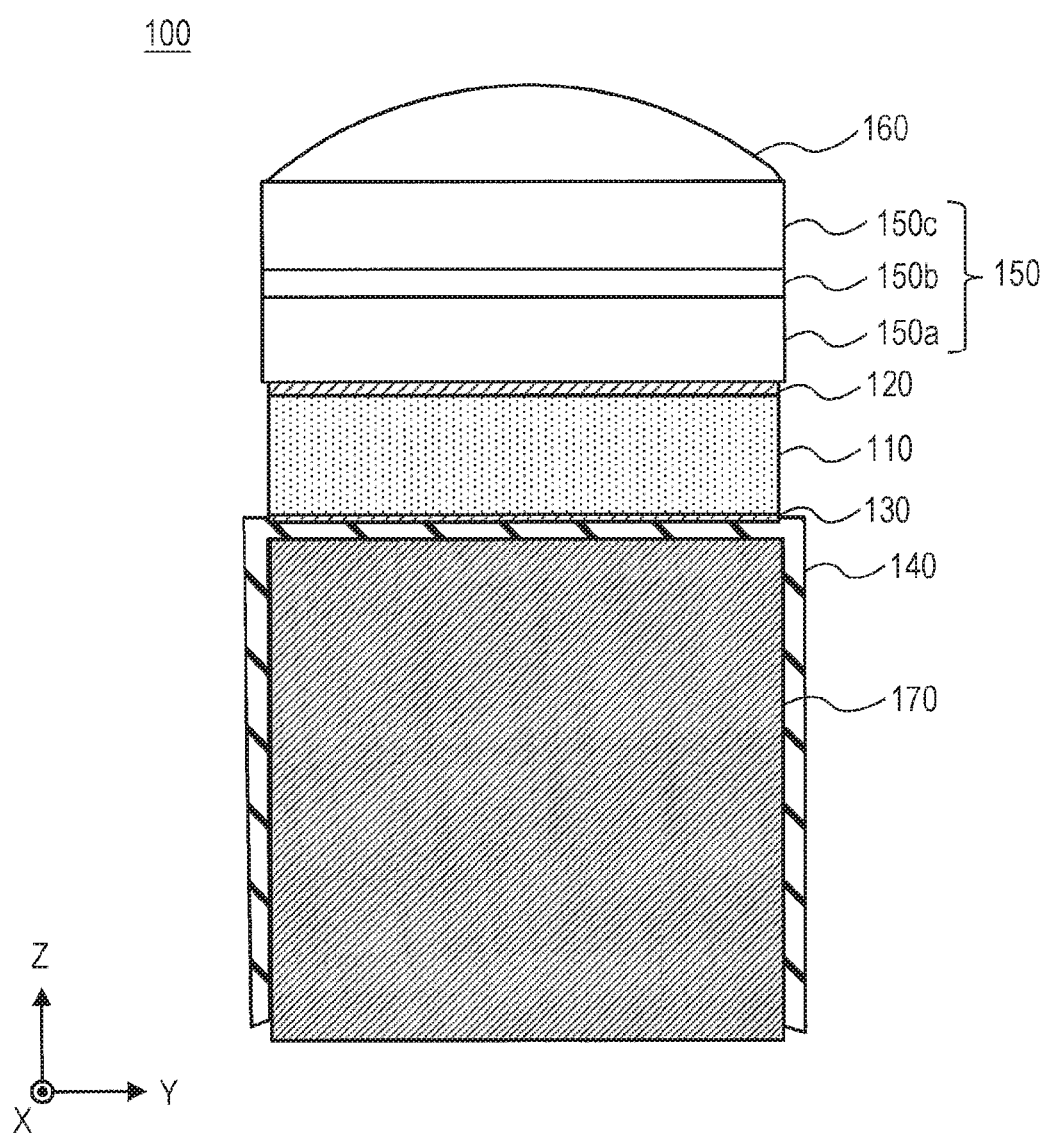
FIG. 1 is a cross-sectional view illustrating an example of the entire structure of an ultrasonic probe according to an embodiment of the present invention.

FIG. 1 is a cross-sectional view illustrating an example of the entire structure of an ultrasonic probe 100 according to a first embodiment of the present invention.

As illustrated in FIG. 1, the structure of the ultrasonic probe 100 includes an acoustic lens 160, an acoustic matching layer 150 disposed at a rear surface side of the acoustic lens 160, a piezoelectric element 110 disposed at a rear surface side of the acoustic matching layer 150 and used for transmitting and receiving ultrasonic waves, a ground electrode 120 disposed at a front surface side of the piezoelectric element 110, a signal electrode 130 disposed at a rear surface side of the piezoelectric element 110, a signal electric terminal 140, and a backing 170 disposed at a rear surface side of the signal electrode 130.

The piezoelectric element 110 is formed in such a manner that a plurality of piezoelectric bodies (not illustrated), which transmit ultrasonic waves by application of a voltage, are arranged in one dimension in an X direction of FIG. 1. The thickness of the piezoelectric element 110 can be set, for example, to 0.05 mm or more and 0.4 mm or less. Each of the piezoelectric bodies is formed by piezoelectric ceramic such as a lead zirconate titanate (PZT)-based ceramic, a piezoelectric single crystal such as a lead magnesium niobate-lead titanate solid solution (PMN-PT) and lead niobate zincate-lead titanate solid solution (PZN-PT), a composite piezoelectric body formed by those materials and a polymer material, and the like.

The ground electrode 120 is an electrode disposed on the front surface of the piezoelectric element 110, and the signal electrode 130 is an electrode disposed on the rear surface of the piezoelectric element 110. The ground electrode 120 and the signal electrode 130 can be formed by a method such as deposition or sputtering of gold, silver, or the like and silver printing, or can be formed by pasting a conductor such as copper to an insulating substrate to be patterned, or the like. The signal electric terminal 140 is disposed in contact with the rear surface side of the signal electrode 130 and connects the signal electrode 130 and an external power supply or the like disposed on a main body 11 of an ultrasonic diagnostic apparatus 10. In the present embodiment, the signal electrode 130 is a flexible printed circuit (FPC) which is formed by pasting a conductor such as copper to an insulating substrate to be patterned.

The acoustic matching layer 150 is a layer for matching acoustic characteristics between the piezoelectric element 110 and the acoustic lens 160, and is formed by a material having an approximately intermediate acoustic impedance between the piezoelectric element 110 and the acoustic lens 160. In the present embodiment, the acoustic matching layer 150 is formed by three layers of a first acoustic matching layer 150a, a second acoustic matching layer 150b, and a third acoustic matching layer 150c.

In the present embodiment, the first acoustic matching layer 150a is formed by materials such as silicon, crystal, free-machining ceramics, graphite filled with metallic powder, and an epoxy resin filled with a filler such as a metal or an oxide, having an acoustic impedance of 8 MRayls or more and 20 MRayls or less. The second acoustic matching layer 150b is formed by graphite and an epoxy resin filled with a filler such as a metal or an oxide, having an acoustic impedance of 3 MRayls or more and 8 MRayls or less. The third acoustic matching layer 150c is formed by a plastic material mixed with a rubber material, a resin filled with silicone rubber powder, and the like, having an acoustic impedance of 1.9 MRayls or more and 2.3 MRayls or less. When the acoustic matching layer 150 is multi-layered in this way, the ultrasonic probe 100 becomes broad. Incidentally, when the acoustic matching layer 150 is multi-layered, it is more preferable to set an acoustic impedance of each layer such that the acoustic impedance gets gradually or continuously closer to the acoustic impedance of the acoustic lens 160 as the acoustic matching layer approaches the acoustic lens 160. Further, the respective layers of the multi-layered acoustic matching layer 150 may be bonded with an adhesive, which is generally used in the concerned technical field, such as an epoxy-based adhesive.

Incidentally, the materials of the acoustic matching layer 150 are not limited to the above-described materials, and known materials including aluminum, aluminum alloy, magnesium alloy, Macor glass, glass, fused quartz, copper graphite, resins, and the like can be used. Examples of the resins include polyethylene, polypropylene, polycarbonate, an ABS resin, an AAS resin, an AES resin, nylon, polyphenylene oxide, polyphenylene sulfide, polyphenylene ether, polyetheretherketone, polyamide imide, polyethylene terephthalate, an epoxy resin, and a urethane resin.

The acoustic lens 160 is formed, for example, by a soft polymer material or the like which has an acoustic impedance close to the living body and an acoustic velocity different from the living body, and the acoustic lens 160 converges ultrasonic waves transmitted from the piezoelectric element 110 using refraction due to a difference in acoustic velocity between the living body and the acoustic lens 160 to improve resolution. In the present embodiment, the acoustic lens 160 is a cylindrical acoustic lens 160 which extends along a Y direction in the drawing (a direction perpendicular to an arrangement direction X of the piezoelectric body) and is formed in a convex shape in a Z direction. The acoustic lens 160 converges the ultrasonic waves in the Y direction to output the ultrasonic waves outside the ultrasonic probe 100.

Examples of the soft polymer material include silicone rubber.

The backing 170 is a layer that holds the piezoelectric element 110 and attenuates ultrasonic waves transmitted from the piezoelectric element 110 to the rear surface side. The backing 170 is generally formed by synthetic rubber, natural rubber, an epoxy resin, a thermoplastic resin, or the like which is filled with a material for adjusting an acoustic impedance. The shape of the backing 170 is not particularly limited as long as it can attenuate the transmitted ultrasonic waves.

The signal electrode 130 as FPC is disposed on the backing 170, and further, the piezoelectric element 110 is disposed with the signal electrode 130 (FPC) interposed between the piezoelectric element 110 and the backing 170 so as to face the backing 170. Herein, the area of the surface of the backing 170 being in contact with the piezoelectric element 110 is preferably larger than that of the piezoelectric element 110.

In the backing 170, it is demanded to achieve both of radiating of heat generated from the piezoelectric element 110 to the rear surface side and attenuating of ultrasonic waves transmitted from the piezoelectric element 110 to the rear surface side. Herein, in order to further increase a radiation amount, the thermal resistance of the backing 170 is necessary to decrease, and in order to decrease the thermal resistance, the backing 170 is necessary to form thinner. Meanwhile, in order to further increase an attenuation amount of ultrasonic waves, the backing 170 is necessary to form thicker. As such, it is difficult to achieve both of further increasing of the radiation amount from the backing 170 and increasing of the attenuation amount of ultrasonic waves in the backing 170.

(Regarding Relation Between Thickness of Backing and Surface Temperature of Acoustic Lens)

Figure 2:
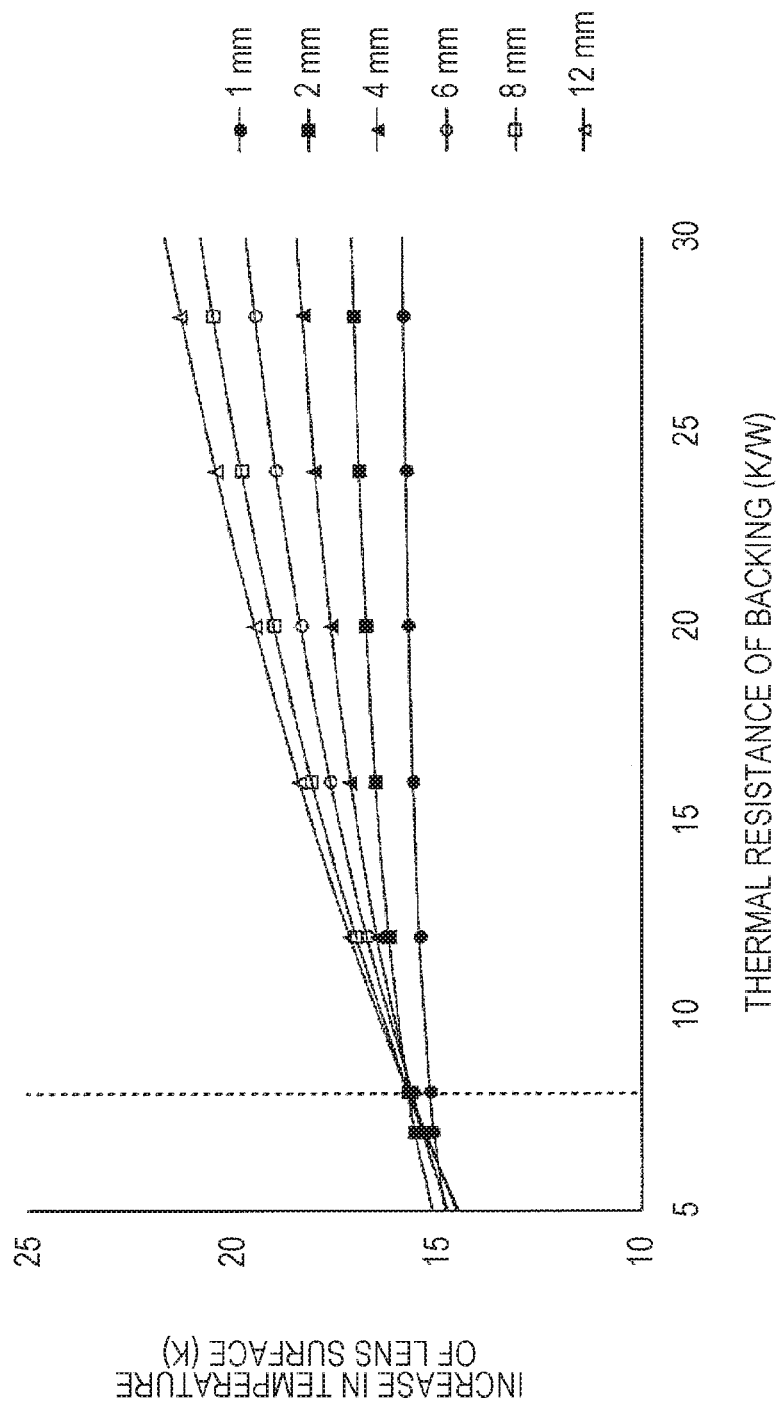
FIG. 2 is a graph showing a relation between an increase in temperature of a lens surface and a thermal resistance caused by a difference in thickness of a backing.

FIG. 2 is a graph showing a relation between an increase in temperature of a surface of the acoustic lens 160 and a thermal resistance caused by a difference in thickness of the backing 170. Herein, the ordinate in FIG. 2 represents an increase in temperature (K) of the surface of the acoustic lens 160 and the abscissa represents a thermal resistance (K/W) of the backing 170.

Herein, the term "thermal resistance" refers to an amount that is determined by the shape (thickness and contact area) and the thermal conductivity of the backing 170. That is, as the thermal resistance of the backing 170 decreases (the thickness of the backing 170 decreases), a voltage used in transmission of ultrasonic waves can be increased.

In FIG. 2, the thicknesses of the backing 170 are set to 1, 2, 4, 6, 8, and 12 mm, the thermal resistance in respective thicknesses of the backing 170 are set to 1, 4, 8, 12, 16, 20, 24, 28, and 32 K/W, and then the amount of increase in temperature of the surface of the acoustic lens 160 in each thickness and thermal resistance (as the amount of increase in temperature decreases, the radiation amount of the backing 170 increases) is checked. Of these, the abscissa in FIG. 2 represents the thermal resistance of 5 to 30 K/W. Even in any thickness of the backing 170, by decreasing the thermal resistance of the backing, the increase in temperature of the surface of the acoustic lens 160 is suppressed. In particular, when the thermal resistance of the backing 170 becomes 8 K/W or less, it is found that, regardless of the thickness of the backing 170, the temperature of the surface of the acoustic lens 160 shows almost the same increase in temperature. From this result, by using the backing 170 having a thermal resistance of 8 K/W or less, it is found that the radiation amount does not decrease even when the thickness of the backing 170 is further increased.

(Frequency Characteristics of Sector Probe)

Figure 3:
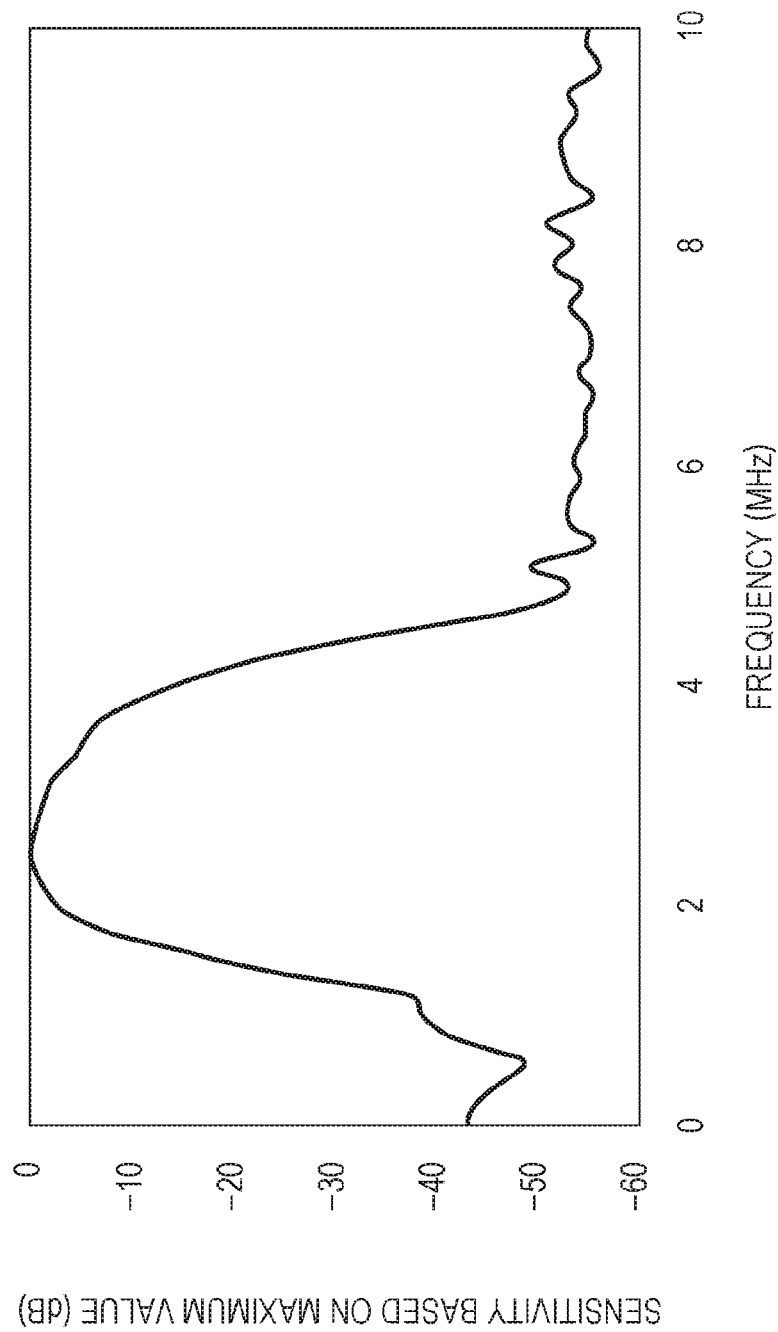
FIG. 3 is a graph showing frequency characteristics of a general low-frequency probe.

FIG. 3 is a graph showing frequency characteristics of a sector probe as a low-frequency probe. Herein, the ordinate in FIG. 3 represents sensitivity (dB) based on the maximum value of transmittance and reception sensitivity and the abscissa represents a frequency (MHz).

In FIG. 3, the ordinate represents a sensitivity (dB) based on the maximum value of transmittance and reception sensitivity, the maximum value is 0, and the minimum value is −60. Further, the abscissa represents a frequency (MHz), the minimum value is 0, and the maximum value is 10. In ultrasonic diagnosis, in order to obtain an ultrasonic image with a high image quality, it is desirable to generate an ultrasonic image using a frequency at which the sensitivity is −20 or more. Herein, the sector probe is mainly used in inspection of a circulatory organ and abdomen. In particular, in a mode for observing the state of blood flow (for example, a color Doppler method, a pulse Doppler method, or the like), the transmittance and reception sensitivity of the ultrasonic probe in low-frequency waves becomes important. For this reason, it is desirable to improve the transmittance and reception sensitivity of ultrasonic waves in a low-frequency region (1.5 to 4.2 MHz) within a range in which the transmittance and reception sensitivity is decreased from the maximum value by 20 dB as described above.

Therefore, in the present embodiment, in order to enhance the image quality of the ultrasonic image by low-frequency ultrasonic waves, it is desirable that the attenuation amount of the backing 170 with respect to an ultrasonic wave with the lowest frequency, among frequencies at which the sensitivity is −20 or more, is larger. Specifically, in the present embodiment, the backing 170 attenuates the ultrasonic wave with the lowest frequency by 10 dB or more.

(Backing)

In the present embodiment, by appropriately increasing the thermal conductivity of the backing 170, the thermal resistance of the backing 170 is set to 8 K/W or less and the thickness of the backing 170 is set to such a thickness that the ultrasonic wave with the lowest frequency is attenuated by 10 dB or more. For example, in order to increase the thermal conductivity, the backing 170 preferably contains a base material and a thermally conductive filler. Further, in order to adjust the acoustic impedance of the backing 170 and improve the transmission sensitivity of the ultrasonic probe 100, hollow particles are preferably contained.

Examples of the base material include natural rubber, ferrite rubber, an epoxy resin, and a thermoplastic resin. In the present embodiment, an epoxy resin is preferable. Examples of the epoxy resin include novolac type epoxy resins such as bisphenol A type, bisphenol F type, resol novolac type, and phenol modified novolac type epoxy resins; polycyclic aromatic epoxy resins such as naphthalene structure-containing type, anthracene structure-containing type, and fluorene structure-containing type epoxy resins; hydrogenated alicyclic epoxy resins, and liquid-crystalline epoxy resins. The epoxy resin may be used alone or in combination of two or more kinds thereof. The shape of the backing 170 may be appropriately designed depending on the shape of the piezoelectric element 110 or the shape of the ultrasonic probe 100.

Further, a reactive diluent may be added to the base material. Examples of the reactive diluent include butyl glycidyl ether, 2-ethylhexyl glycidyl ether, phenyl glycidyl ether, orthocresyl glycidyl ether, 1,4-butanediol diglycidyl ether, 1,6-hexanediol diglycidyl ether, propylene glycol diglycidyl ether, and diethylene glycol diglycidyl ether. The reactive diluent may be used alone or in combination of two or more kinds thereof.

In the case of using an epoxy resin in the base material, it is necessary to further add a curing agent. Examples of the curing agent include chain aliphatic polyamines such as diethylene triamine, triethylene tetramine, dipropylene diamine, and diethylaminopropylamine; cyclic aliphatic polyamines such as N-aminoethylpiperazine, mensendiamine, and isophoronediamine; aromatic amines such as m-xylenediamine, meta-phenylenediamine, diaminodiphenylmethane, and diaminodiphenylsulfone; polyamide resins; secondary and tertiary amines such as piperidine, N,N-dimethylpiperazine, triethylenediamine, 2,4,6-tris(dimethylaminomethyl)phenol, benzyldimethylamine, and 2-(dimethylaminomethyl)phenol; imidazoles such as 2-methylimidazole, 2-ethylimidazole, and 1-cyanoethyl-2-undecyl imidazolium trimellitate; liquid polymercaptans and polysulfides; and acid anhydrides such as phthalic anhydride, trimellitic anhydride, methyltetrahydrophthalic anhydride, methyl endomethylene tetrahydrophthalic anhydride, methylbutenyl tetrahydrophthalic anhydride, and methylhexahydrophthalic anhydride. The curing agent may be used alone or in combination of two or more kinds thereof.

Examples of the thermally conductive filler which is added to the base material include graphite, carbon nanotube, silicon carbide, aluminum nitride, boron nitride, copper, and multi-layered graphene (thermal conductivity: 600 to 800 W/m/K). In the present embodiment, multi-layered graphene is preferable. The thermally conductive filler may be used alone or in combination of two or more kinds thereof. By adding the thermally conductive filler, the thermal conductivity of the backing 170 can be adjusted.

Examples of the hollow particles which are added to the base material include Expancel 551DE40d42. The hollow particles may be used alone or in combination of two or more kinds thereof. The acoustic impedance of the backing 170 is adjusted by adding the hollow particles so that the transmission sensitivity of the ultrasonic probe 100 can be improved.

Particularly, in the present embodiment, the thermal conductivity and the acoustic impedance of the backing 170 are adjusted by adding both the thermally conductive filler and the hollow particles so that the transmission sensitivity of the ultrasonic probe 100 can be further improved.

As shown in the following experimental examples, by properly selecting materials, it is possible to manufacture the backing 170 that has a thermal resistance of 8 K/W or less and attenuates an ultrasonic wave with the lowest frequency by 10 dB or more, among frequencies at which transmittance and reception sensitivity of the ultrasonic probe is decreased from the maximum value thereof by 20 dB.

[Experiment 1]
(Production of Backing)

80 parts by mass of base agent A (epoxy resin) "Albidur EP2240: manufactured by NANORESIN, "Albidur" is the registered trademark of NANORESIN" and 24 parts by mass of curing agent D (epoxy resin curing Agent) "jERCURE ST-12: manufactured by Mitsubishi Chemical Corporation, "jERCURE" is the registered trademark of Mitsubishi Chemical Corporation" were mixed, and then 150 parts by mass of thermally conductive filler F (silicon carbide powder) "SSC-A15 (average particle diameter: 19 μm): manufactured by Shinano Electric Refining Co., Ltd." and 125 parts by mass of filler composite particles X (average particle diameter: 215 μm) were added thereto and further mixed to obtain a mixture 1. The filler composite particles X are obtained by mixing liquid silicone rubber (base agent) "TSE3032 (A): manufactured by Momentive Performance Materials Inc.," liquid silicone rubber (curing agent) "TSE3032 (B): manufactured by Momentive Performance Materials Inc.," tungsten oxide "C3-WO3: manufactured by A.L.M.T. Corp.," and spherical silicon carbide "SSC-A30: Shinano Electric Refining Co., Ltd." at 91:9:250:220 (mass ratio).

The mixture 1 was put in a mold having a size of 100 mm×100 mm×30 mm, was left to stand still for 4 hours at room temperature by an electrically heated vacuum pressing machine "OHV-H" (manufactured by Oji Machine Co., Ltd.) in a state of being pressurized at a pressure of 9.9 MPa (100 kg/cm$^2$), and was heated at 60° C. for 3 hours to produce a backing block (density: 2.1 g/cm$^3$, acoustic impedance: 2.5 MRayls, attenuation amount: 7.0 dB/MHz). The backing block was cut by a wire saw "CS-203" (manufactured by Musashino Denshi, Inc.) and was further polished by a precise polishing device "MA-200" (manufactured by Musashino Denshi, Inc.) to have a thickness of 1.3 mm. According to this, a backing block 1 having a thermal resistance of 2.1 K/W was obtained.

[Experiment 2]

A backing block 2 was obtained in a similar manner to Experiment 1, except that the thickness of the backing block was set to 4.9 mm, the density was set to 2.1 g/cm$^3$, the acoustic impedance was set to 2.5 MRayls, the attenuation amount was set to 26.5 dB/MHz, and the thermal resistance was set to 8.0 K/W.

[Experiment 3]

The base agent A (80 parts by mass) of Experiment 1 was changed to 68 parts by mass of base agent B "jER828: manufactured by Mitsubishi Chemical Corporation, "jER" is the registered trademark of Mitsubishi Chemical Corporation," and the curing agent D (24 parts by mass) was changed to 25 parts by mass of curing agent E "jERCURE113: manufactured by Mitsubishi Chemical Corporation." Further, the thermally conductive filler F (150 parts by mass) was changed to 10 parts by mass of thermally conductive filler G "iGurafen-aS: manufactured by iTEC Co., Ltd., "iGurafen" is the registered trademark of iTEC Co., Ltd.," and the filler composite particles X (125 parts by mass) were changed to 205 parts by mass of filler composite particles Y (average particle diameter: 198 μm). Further, 0.4 part by mass of hollow particles Z "Expancel 551DE40d42: manufactured by AkzoNovel, "Expancel" is the registered trademark of AkzoNovel" were added. A backing block 3 was obtained in a similar manner to Experiment 1, except that the thickness of the backing block was set to 1.7 mm, the density was set to 1.8 g/cm$^3$, the acoustic impedance was set to 2.3 MRayls, the attenuation amount was set to 7.0 dB/MHz, and the thermal resistance was set to 0.6 K/W. The filler composite particles Y are obtained by mixing liquid silicone rubber (base agent) "TSE3032 (A) (manufactured by Momentive Performance Materials Inc.)," liquid silicone rubber (curing agent) "TSE3032 (B) (manufactured by Momentive Performance Materials Inc.)," tungsten oxide "C3-W03 (manufactured by A.L.M.T. Corp.)," and graphene "iGurafen-aS (manufactured by iTEC Co., Ltd.)" at 91:9:420:53 (mass ratio).

[Experiment 4]

A backing block 4 was obtained in a similar manner to Experiment 3, except that the thickness of the backing block was set to 22.1 mm, the density was set to 1.8 g/cm$^3$, the acoustic impedance was set to 2.3 MRayls, the attenuation amount was set to 90.6 dB/MHz, and the thermal resistance was set to 8.0 K/W.

[Experiment 5]

The filler composite particles X (125 parts by mass) were changed to 380 parts by mass of filler composite particles W (average particle diameter: 116 μm). A backing block 5 was obtained in a similar manner to Experiment 1, except that the thickness of the backing block was set to 0.5 mm, the density was set to 2.6 g/cm$^3$, the acoustic impedance was set to 2.7 MRayls, the attenuation amount was set to 3.8 dB/MHz, and the thermal resistance was set to 8.0 K/W. The filler composite particles W are obtained by mixing liquid silicone rubber (base agent) "TSE3032 (A): manufactured by Momentive Performance Materials Inc.," liquid silicone rubber (curing agent) "TSE3032 (B): manufactured by Momentive Performance Materials Inc.," and tungsten oxide "C3-WO3: manufactured by A.L.M.T. Corp." at 91:9:730 (mass ratio).

The composition elements and the composition ratios of the backing blocks 1 to 5 are presented in Table 1.

TABLE 1

| Backing block | Base material | | | Thermally conductive filler | | Filler composite particles | | Other filler | |
|---|---|---|---|---|---|---|---|---|---|
| | Base agent (parts by mass) | Reactive diluent (parts by mass) | Curing agent (parts by mass) | Type | Added amount (parts by mass) | Type | Added amount (parts by mass) | Type | Added amount (parts by mass) |
| Experiment 1 | A (80) | — | D (24) | F | 150 | X | 125 | — | — |
| Experiment 2 | A (80) | — | D (24) | F | 150 | X | 125 | — | — |
| Experiment 3 | B (68) | C (8) | E (25) | G | 85 | Y | 205 | Z | 0.4 |
| Experiment 4 | B (68) | C (8) | E (25) | G | 85 | Y | 205 | Z | 0.4 |
| Experiment 5 | A (80) | — | D (24) | — | — | W | 380 | — | — |

The physical property values of the backing blocks 1 to 5 are presented in Table 2.

TABLE 2

| Backing block | Density (g/cm$^3$) | Acoustic impedance (MRayls) | Thickness (mm) | Thermal resistance (K/W) | Attenuation (dB/MHz) | Attenuation (dB) |
|---|---|---|---|---|---|---|
| Experiment 1 | 2.1 | 2.5 | 1.3 | 2.1 | 7.0 | 10.5 |
| Experiment 2 | 2.1 | 2.5 | 4.9 | 8.0 | 26.5 | 39.7 |
| Experiment 3 | 1.8 | 2.3 | 1.7 | 0.6 | 7.0 | 10.5 |
| Experiment 4 | 1.8 | 2.3 | 22.1 | 8.0 | 90.6 | 135.9 |
| Experiment 5 | 2.6 | 2.7 | 0.5 | 8.0 | 3.8 | 5.7 |

As shown in Experiments 1 to 4, it is found that by containing the thermally conductive filler in the base material, as compared to Experiment 5 (no thermally conductive filler), a favorable attenuation amount is obtainable. Particularly, as comparing the backing blocks of Experiment 2 and Experiment 5 in which the thermal resistance was set to 8 K/W to each other, it is found that by containing the thermally conductive filler in the base material in Experiment 2, a favorable attenuation amount is obtainable even when the backing block is thick. Further, as comparing the backing blocks of Experiment 4 and Experiment 5 in which the thermal resistance was set to 8 K/W to each other, it is found that by containing the thermally conductive filler and the hollow particles in the base material in Experiment 4, the acoustic impedance can be adjusted, and favorable radiation characteristics having a thermal resistance of 8 K/W or less are obtainable even when the backing block is thick. Therefore, even in the structure in which the reflecting layer is not provided at the rear surface side of a piezoelectric plate, a backing having sufficient radiation properties can be obtained without degradation in diagnostic image occurring. Further, since the radiation amount is not decreased even when the thickness of the backing increases, the adjustment of the attenuation amount can be performed by adjusting the thickness of the backing 170.

As described above, in the ultrasonic probe of the present invention, attenuation can be adjusted to 10 dB or more even in a case where the thermal resistance is set to 8 K/W or less.

The backing 170 may have a thermally conductive material at the rear surface side of the backing 170 or in the periphery thereof. Examples of the thermally conductive material include metals such as aluminum, copper, and magnesium, graphite, and multi-layered graphene.

Further, the backing 170 may have a thermally conductive potting material at the rear surface side thereof. Examples of the potting material include liquid silicone rubber, an epoxy resin, and materials obtained by mixing a thermally conductive filler such as aluminum oxide in those materials.

The ultrasonic probe 100 may have a window (not illustrated) that is a protection member for protecting the piezoelectric element 110 or the like from a pressure caused by contact with the living body, at a position, which covers a side being in contact with a subject, of the ultrasonic probe 100. Further, the ultrasonic probe 100 may have an acoustic medium liquid (not illustrated) for acoustically matching the window and the transmission and reception surface of the piezoelectric element 110, between the window and the acoustic lens 160, or the like.

Further, the ultrasonic probe 100 may have a swing mechanism (not illustrated) for swinging the piezoelectric element 110 to scan the ultrasonic signal, at the rear surface side of the backing 170. Furthermore, the ultrasonic probe 100 may have an acoustic reflecting layer (not illustrated) at the rear surface side of the piezoelectric element 110.

In the ultrasonic probe 100, the thermal conductor and a housing (not illustrated) of the ultrasonic probe 100 may be connected by a thermally conductive material. Examples of the thermal conductor include metals such as aluminum, copper, and magnesium, graphite, and multi-layered graphene. Further, examples of the thermally conductive material include metals such as aluminum, copper, and magnesium, graphite, and multi-layered graphene. Furthermore, the housing of the ultrasonic probe 100 may have a thermal conductor in a direction along the housing. At this time, the housing and the thermal conductor may be in contact with each other or may be separated from each other.

(Ultrasonic Diagnostic Apparatus)

Figure 4:
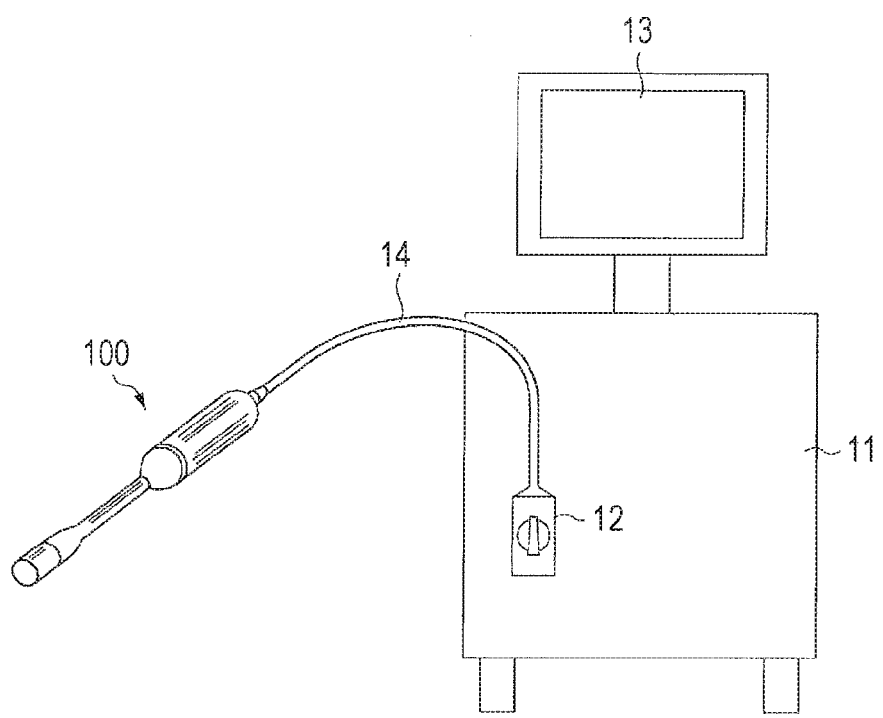
FIG. 4 is a schematic diagram illustrating an example of an ultrasonic diagnostic apparatus provided with an ultrasonic probe according to an embodiment of the present invention.

FIG. 4 is a schematic diagram illustrating an example of the ultrasonic diagnostic apparatus 10 provided with the ultrasonic probe 100. The ultrasonic diagnostic apparatus 10 includes the ultrasonic probe 100, the main body 11, a connector 12, and a display 13.

The ultrasonic probe 100 is connected to the ultrasonic diagnostic apparatus 10 through a cable 14 connected to the connector 12.

The electric signal (transmission signal) from the ultrasonic diagnostic apparatus 10 is transmitted to the piezoelectric element 110 of the ultrasonic probe 100 through the cable 14. This transmission signal is converted into ultrasonic waves in the piezoelectric element 110 and the ultrasonic waves are transmitted in the living body. The transmitted ultrasonic waves are reflected by tissues or the like in the living body, some of reflected waves are received in the piezoelectric element 110 to be converted into an electric signal (reception signal), and the electric signal is transmitted to the main body 11 of the ultrasonic diagnostic apparatus 10. The reception signal is converted into image data in the main body 11 of the ultrasonic diagnostic apparatus 10 and the image data is displayed on the display 13.

The ultrasonic diagnostic apparatus of the present invention can generate an ultrasonic image with a favorable image quality since the ultrasonic probe of the present invention is provided.

According to an embodiment of the present invention, the ultrasonic probe is useful as an ultrasonic probe of an ultrasonic apparatus which is intended to obtain an ultrasonic image with excellent sensitivity and a favorable image quality in a low-frequency region.

Although embodiments of the present invention have been described and illustrated in detail, the disclosed embodiments are made for purposes of illustration and example only and not limitation. The scope of the present invention should be interpreted by terms of the appended claims.

What is claimed is:

1. An ultrasonic probe comprising:
    a piezoelectric element that is used for transmitting and receiving ultrasonic waves;
    a signal electrode that is disposed at a rear surface side of the piezoelectric element; and
    a backing that is disposed at a rear surface side of the signal electrode,
    wherein the backing material is formed from a mixture containing a base material mixed with a thermally conductive filler material,
    the backing has a thermal resistance of 8 K/W or less, and
    the backing attenuates an ultrasonic wave with the lowest frequency by 10 dB or more, among frequencies at which transmittance and reception sensitivity of the ultrasonic probe is decreased from the maximum value thereof by 20 dB.

2. The ultrasonic probe according to claim 1, wherein the mixture from which the backing is formed further contains hollow particles.

3. An ultrasonic diagnostic apparatus comprising the ultrasonic probe according to claim 1.

4. The ultrasonic probe according to claim 1, wherein the base material is selected from the group consisting of natural rubber, ferrite rubber and an epoxy resin.

5. The ultrasonic probe according to claim 1, wherein the backing has a damping ratio of 26.5 dB/MHz or more.

6. The ultrasonic probe according to claim 1, wherein the mixture from which the backing is formed includes particles of the base material mixed with particles of the thermally conductive filler material.

* * * * *